United States Patent
Bondar et al.

(10) Patent No.: US 8,105,297 B2
(45) Date of Patent: Jan. 31, 2012

(54) DRAINAGE

(76) Inventors: Grygoriy Bondar, Doneck (UA);
Gennadiy Psaras, Mariupol (UA);
Oleksandr Bondar, Doneck (UA);
Oleksandr Zaika, Doneck (UA);
Volodimir Savran, Lviv (UA)

( * ) Notice: Subject to any disclaimer, the term of this patent is extended or adjusted under 35 U.S.C. 154(b) by 690 days.

(21) Appl. No.: 12/286,388

(22) Filed: Sep. 30, 2008

(65) Prior Publication Data

US 2009/0264841 A1  Oct. 22, 2009

(30) Foreign Application Priority Data

Apr. 21, 2008 (UA) .................................. 200805098

(51) Int. Cl.
*A61M 1/00* (2006.01)
(52) U.S. Cl. ........ 604/319; 604/318; 604/320; 604/321; 604/322; 604/323; 604/324; 604/19; 604/27; 604/48; 604/93.01; 604/96.01; 604/101.01; 604/158; 604/161; 604/4.01; 604/174; 604/264; 604/272; 604/540; 606/108
(58) Field of Classification Search .................. 604/318, 604/319, 321, 323
See application file for complete search history.

(56) References Cited

U.S. PATENT DOCUMENTS

| | | | |
|---|---|---|---|
| 3,978,863 A * | 9/1976 | Fettel et al. .................... | 606/194 |
| 7,322,958 B2 * | 1/2008 | Wholey et al. ............ | 604/102.01 |
| 7,364,562 B2 * | 4/2008 | Braig et al. .................. | 604/6.08 |
| 7,857,781 B2 * | 12/2010 | Noda et al. .................... | 604/6.13 |
| 2007/0106211 A1 * | 5/2007 | Provost-Tine et al. ..... | 604/96.01 |

FOREIGN PATENT DOCUMENTS

RU  2066207  9/1996

OTHER PUBLICATIONS

V.G.Ivshin An appliance for drainage of cavity formation via skin // Surgery—1998.—No. 8.—p. 49-50.,, (Abstract and identification of References only).
A.M.Moroz Drainage tube with centimeters points // Clinical surgery.—1969.—No. 5—p. 35 (Abstract and identification of References only).
V.I. Shaposhnikov—A design of a drainage tube of a prolong action // Vestnik Khirurghii (Messenger of Surgery).—2002.—No. 5—p. 81-83. (Abstract and identification of References only).

* cited by examiner

*Primary Examiner* — Tatyana Zalukaeva
*Assistant Examiner* — Ilya Treyger
(74) *Attorney, Agent, or Firm* — Yefim Kreydin (57) ABSTRACT

Drainage belongs to medical equipment, particularly to medical tools and is specified for drainage of cavities. Drainage comprises a first tube, an additional tube, which is fixed upon it, a unit of the clot's splitter and the splitter's fixing element. The additional tube has a smaller diameter with an opening, inside which the conductor is mounted, a unit of clots splitter is installed on the working end of the drainage, it comprises a cylinder, a tube with an opening, placed on it, which is the continuation of the additional tube of the drainage and a spring with a cutter inside the cylinder. A cutter is located diametrically inside the working head, while in the end of the wall of the first tube and the splitter's unit comprises a channel, inside which splitter's fixing element was led, its working end is inside the unit's cylinder and fixes the splitter. This design ensures the permeability of the wound channel after the drainage is removed and it is possible to reinstall drainage into the cavity strictly along the existing wound channel.

6 Claims, 12 Drawing Sheets

DRAINAGE

This application is the United States national phase application of Ukrainian Patent Application No. 2008 05098 filed Apr. 21, 2008 incorporated therein by reference.

FIELD OF THE INVENTION

The presented technical solution deals with medical equipment, particularly with tools for surgery and is specified for draining of cavities after various types of surgical operations.

BACKGROUND OF THE INVENTION

In surgery a necessity of long draining of cavities often arises. Drainage of various designs is used for this purpose, the appliances are inserted into the drained cavity, ensuring active or passive aspiration. The main and so far unsolved problem of prolong drainage of cavities remains maintaining of permeability of drainage and ensuring the natural process of gradual constriction of wound channel as the cavity heals. Unfortunately despite constant perfection of the design of drainage systems, the drainage opening after some time is obturated with fibrin's clot. In this case drainage is removed and a new drainage system is installed into the drained cavity. Unfortunately it is practically impossible to insert a new drainage into the drained cavity using the old wound passage. This is explained by two main reasons. Firstly, the wound passage is of winding shape on the spot of the removed drainage system and it is practically impossible to lead a new drainage through all its turns. Secondly, fibrin's clots that are found inside the passage of the removed drainage is fixed inside the cavity and is partially preserved inside the passage of the wound channel after the drainage system is removed. The remaining clots prevent insertion of a new drainage strictly along the old wound channel, it may be infected and promote inflammatory process inside the wound channel, decelerating the healing of the cavity and the wound channel. In such cases in order to obtain prolong drainage of cavities an old drainage is removed after it has been obturated with fibrin clots and a new drainage system is installed, using a new wound channel. Several problems arise here. Firstly, it is impossible to lead a new drainage along a new passage strictly to the spot where the end of the old drainage was, thus making the process of cavity's draining inadequate. Secondly, formation of a new wound channel will further traumatize the tissues and may provoke generalization of the infection inside the drained cavity. Thirdly, the presence of fibrin clot inside the old wound channel will promote the inflammatory process inside it.

The appliance for drainage of cavities through skin is known [V. G. Ivshin An appliance for drainage of cavity formation via skin//Surgery—1998.—No 8.—p. 49-50.], this appliance presents a needle with an external cannula, installed non-stationary upon it and drainage to be inserted into the drained cavity along a new wound channel, supervised by ultrasonic testing.

The drawback of this system is impossibility of its insertion along the old wound channel and the necessity to use expensive and technically complicated equipment.

Another design includes drainage tube [A. M. Moroz Drainage tube with centimeters points//Clinical surgery.—1969.—No 5—p. 35.], which presents a spherically closed end of children stomach pump. Before application all necessary holes are made in the tube and it is inserted into the desired depth. According to its author this tube can easily be substitutes, by means of a metal mandrel.

The main drawback of the drainage tube of such design is the absence of a butt hole, thus making the process of drainage ineffective. It is not possible to reinstall the drainage, using a mandrel, as specified by the author.

A model of a drain tube, functioning for a long time is also known [V.I. Shaposhnikov—A design of a drainage tube of a prolong action//Vestnik Khirurghii (Messenger of Surgery).—2002.—No 5—p. 81-83.], it was chosen as prototype which specifies the possibility of regulating the permeability of drainage by inserting a bead fixed on a fishing line, both ends of the line are drawn outside. By means of constant drawing of the bead backwards and forwards along the tube's body constant destruction of fibrin clots, precipitated into the drainage passage is performed, due to traction on the line's ends. The authors also specify periodic shift of the drainage system alongside its length, within 1-2 cm, 4-6 times a day.

The drawback of this design, chosen as a prototype is the necessity of location of both ends outside, thus making it impossible to apply it in the bulk of clinical situations, when drainage has to be inserted from one side only. Besides, the drained cavity may get infected when the bead is moved, through a piece of fishing line that was led outside. An organizational difficulty of application of such type of drainage that supposes constant bandaging (up to 6 times a day) may be considered another drawback.

The present invention solves the problem of ensuring the possibility of removing the clot inside the drainage opening, but fixed by one end inside the wound cavity during the drainage removal, as well as ensuring the possibility of reinstallation of the drainage with smaller inside diameter, strictly along the old wound channel, irrespective of length and direction of the latter.

SUMMARY OF THE INVENTION

The problem set is solved by fixing an additional tube of smaller diameter with an opening on a tube draining along its entire length, and upon the working end of drainage a unit for clot's destruction is installed, consisting of a cylindrical body, a tube with an opening, an opening, corresponding to an opening of an additional drainage tube and a spring with a splitter, located inside the body, the drainage having a working head with a diametrically located line inside it, connected by means of thread with the body of the splitter, besides inside the wall of the tube drainage and the splitter's unit a channel is made, inside of which there is a fixing unit of the splitter, the working end of which is inside the body of the splitter's unit and it fixes the splitter, while its opposite end is drawn to the outside surface of the drainage through the aforesaid channel and is equipped with a ring. The body of splitter's unit has an internal growing-through from on one side and an external growing-through from the other side, it is also equipped with internal thread on the side of the internal growing-through for ½ of its length, while the diameter of the body in the spot of the external growing-through is equal to the internal diameter of the tube drainage. The channel of splitter's fixing unit, inside the tube drainage and the channel of splitter's fixing unit inside the wall of the body of clots' splitting unit are located on the side, opposite to the place of fixation of an additional tube and the tube of the splitter's unit respectively, the channel of splitter's fixing unit, inside the body of the splitter is opened with an internal opening upon the surface of ledge's ring, formed by the difference between the diameter of the internal growing-through and the internal diameter of the body. The external diameter of the spring is equal to the internal diameter of the splitter's unit, while the diameter and the height of the fixing unit of the spring are equal to the width and depth of the body's slot, respectively. Clots' splitter is fixed to the spring in such a way, so that its axis is located at 90° angle with regard to the axis of the spring's fixing unit's, the protruding end of clots' splitter corresponds to the width of ring's ledge, formed by the difference between the diameter of the internal growing through and the internal diameter of the body, there being a possibility of its turning inside the body at the level of internal growing-through. The working head is made with an external growing-through, equipped with external thread for internal thread of the unit of clots' splitter, the length of the external growing-through being equal to ½ of the length of the internal growing-through of the unit of clots' splitter. The conductor is equipped with a plate and a handle and it has the working and directing ends, both ends being round in shape, while the conductor's plate is installed at 1.5-2.0 mm distance from the butt of the directing end of the conductor. The external surface of the tube drainage possesses slots with latches for the conductor and the fixing element of the splitter, respectively.

The novelty of this design is in the fact that the device ensures permeability of the wound channel after drainage is removed by means of clots removal from the drainage opening, clots being fixed by one end inside the wound's cavity, and by fixing such clots inside drainage. The new drainage may be reinstalled into the drained cavity strictly along the previously formed channel up to the healing of the latter.

BRIEF DESCRIPTION OF THE DRAWINGS

The essence of the presented technical solution is illustrated with the drawings, where:

FIG. 5a presents the cross section view of the tube drainage 5a,

DETAILED DESCRIPTION OF THE INVENTION

All drawings bear the same numbers for:

1—the tube drainage; 2—an additional tube; 3—the unit of clots splitter; 4—the working head; 5—the conductor; 6—the fixing element of the splitter; 7—the working end of the tube drainage; 8—the drainage openings; 9—the opening of the additional tube; 10—splitter's fixing element's channel inside the wall of the tube drainage; 11—the opening of the channel of the splitter's fixing element on the external surface of the tube drainage; 12—the opening of the channel of the fixing element in the butt of the tube drainage; 13—fixing plates; 14—holes, made in fixing plates; 15—the slot for the conductor, made on the external surface of the tube drainage; 16—the slot for the clots splitter's fixing element, made on the external surface of the tube drainage; 17—growing-through of the additional tube, corresponding to the slot for the conductor; 18—the latch, installed in the slot for the conductor; 19—the latch installed in the slot for the fixing element of the splitter; 20—the body of the clots splitter unit; 21—the tube of the clots splitter unit; 22—the opening in the tube of the clots splitter unit; 23—the internal growing-through of the clots splitter unit; 24—the internal thread of the internal growing-through of the clots splitter unit; 25—the external growing-through of the clots splitter unit; 26—the slot of the clots splitter unit; 27—the channel of the splitter's fixing element, made inside the wall of the body of the clots splitter unit; 28—the opening of the channel of the body of the clots splitter unit from the side of the growing-through; 29—the ring of the ledge, formed by the difference between the diameter of the internal growing through and the internal diameter of the body of the clots splitter unit; 30—the opening in the channel of the body of the clots splitter unit; pictured from the side of the external growing-through; 31—the spring; 32—clots splitter; 33—spring's fixing element; 34—the protruding end of the clots splitter; 35—the beveled end of the working head; 36—the external growing-through of the working head; 37—the external thread on the external growing-through of the working head; 38—the rod of the working head; 39—the conductor's working end; 40—the leading end of the conductor; 41—the conductor's plate; 42—the conductor's plate handle; 43—the working end of the splitter's fixing element; 44—the splitter's fixing element's ring; 45—direction of turning of the clots splitter, when it is transferred into the working position; 46—direction of turning of the clots splitter after the splitter's fixing element is removed.

The presented drainage design (See FIG. 1-9, 36) consists of the tube drainage 1, an additional tube 2, fixed upon it, the unit of clots splitter 3, the working head 4, the conductor 5 and the splitter's fixing element 6.

Six openings for drainage, of oval shape 8, three on each side are made on the side surfaces of the tube drainage 1 (FIG. 3) on the side of its working end 7. Along the entire length of the additional tube 2 (FIGS. 3-5a) an opening 9 was made. Inside the wall of the tube drainage 1 on the side opposite to the spot where the additional tube is fixed 2 a channel 10 of the splitter's fixing element 6 was made (FIGS. 51, 5b), which is opened on one side by a hole 11 on the external surface of the tube drainage 1, and by a hole 12 on the side of the working end 12 on the butt end of the tube drainage 1. Two fixing plates 13 (FIG. 5, 5a, 6-8) with two holes 14 in each are fixed on the external surface of the tube drainage 1, on the side, opposite to the working end 7. Besides the external surface of the tube drainage 1 has the slot 15 for the conductor 5 and the slot 16 for the clots splitter's fixing element (FIGS. 5b, 6-8). The additional tube 2 also possesses growing-through 17 (FIGS. 6, 9), corresponding to the slot 15 for the conductor 5. The slot 15 for the conductor 5 has a latch 18 (FIGS. 6, 9), and a latch 19 (FIGS. 8, 9) is installed in the slot 16 for the splitter's fixing element 6.

Clots splitter's unit 3 consists of a body 20, a tube placed on its surface 21, with an opening 22 (FIGS. 10-15). The tube of the clots splitter's unit 21 is the continuation of the additional tube 2, having the same diameter, while the opening 22 of the tube 21 of the clots splitter's unit 21 coincides with the opening 9 of the additional tube 2. Besides, the body 20 has got on one side an internal growing-through 23 with internal thread 24 for ½ of its length. On the other side of the body 20 there is an external growing-through 25, the external diameter of the body 20 in the area of the external growing-through 25 being equal to the internal diameter of the tube drainage 1. A slot 26 is made on the internal surface of the body 20, on the side of the tube's fixing 21, while on the opposite side a channel 27 is made inside the wall of the body for the splitter's fixing element, being the continuation of the channel 10 of the splitter's fixing element, made inside the wall of the tube drainage. The channel 27 is opened by the hole 28 on the ledge's ring 29, which is formed by the difference in the diameter of the internal growing-through 23 and the internal diameter of the body 20. The channel 27 ends on the side of the external growing-through 25 with an opening 30, the diameter of which is equal to the diameter of the opening 12 of the channel of the fixing element in the butt of the tube drainage 1. The unit of the clots splitter also contains the spring 31 with clots splitter 32 and the spring's fixing element 33 (FIGS. 16-19). The external diameter of the spring 31 is equal to the internal diameter of the body 20, the length of the spring's fixing element 33 being equal to the height of the slot 26 of the body 20. The length of the clots splitter 32 is bigger than the diameter of the spring 31 and it corresponds to the internal diameter of the body 20 in the area of the internal growing-through 23. The axis of the clots splitter 32 is located at 90° angle towards the axis of the spring's fixing element 33. The protruding end 34 of the clots splitter 32 ensures fixing of the spring in the necessary position, by means of the splitters fixing element 6.

The working head 4 (FIGS. 20-23) presents a body with one end beveled at 60° angle on one end 35 and the external growing-through 36, made on the other end, having external thread 37 for internal thread 24 of the internal growing-through 23 of the body 20.

The end beveled at 60° angle 35 of the working head 4 ensures minimal injuring of tissues by the end of the drainage system, installed during an operation and it also minimizes traumas, caused to the wound channel, when a new drainage is inserted. The maximal external diameter of the working head 4 is equal to the external diameter of the tube drainage 1 and its internal diameter is equal to the internal diameter of the tube diameter 1. The external diameter of the working head in the area of the external growing-through 36 is equal to the internal diameter of the body 20 of lots splitter in the area of its internal growing-through 23. Inside the working head 4 a rod 38 is installed diametrically on the side of the external growing-through.

Figure 1:
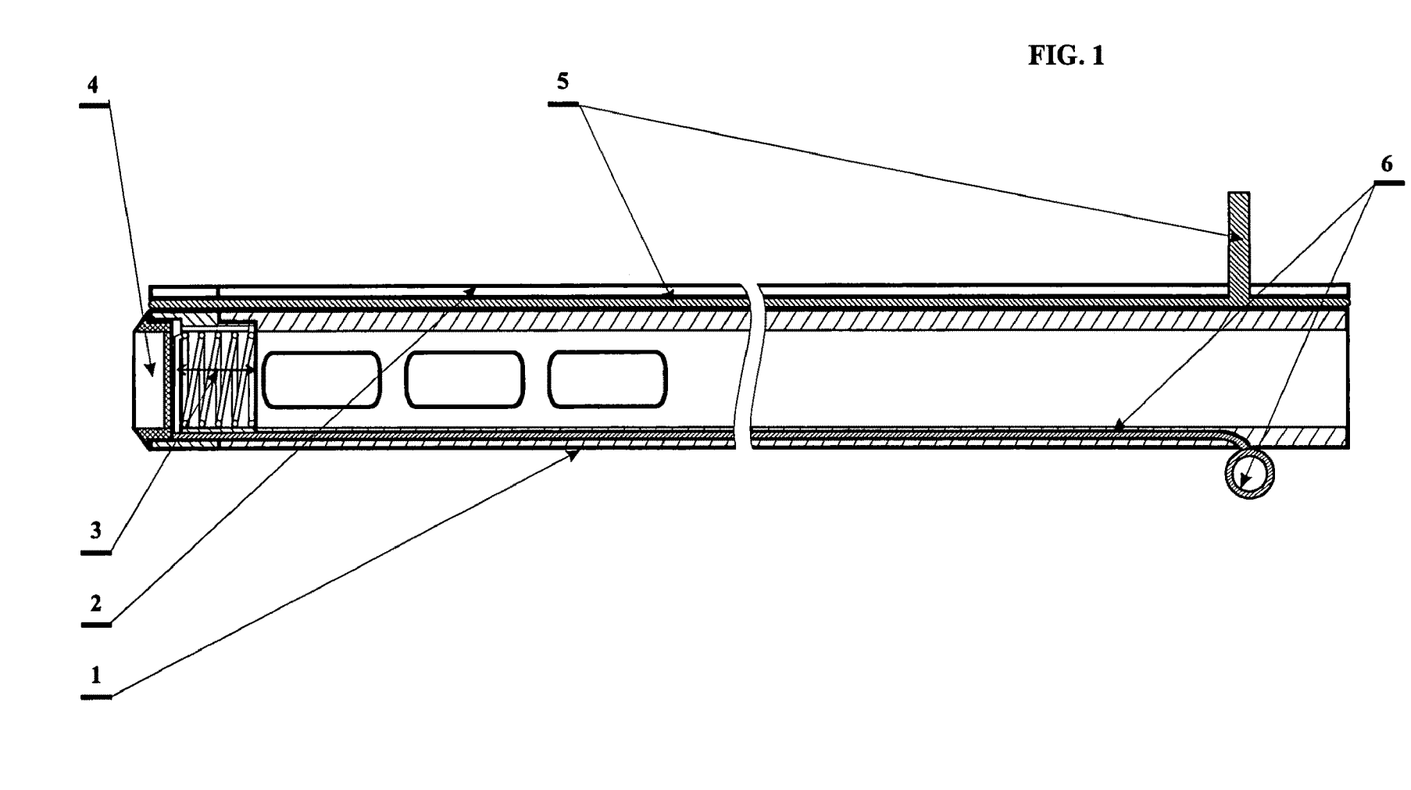
FIG. 1 presents the longitudinal section of the drainage system.
Figure 2:
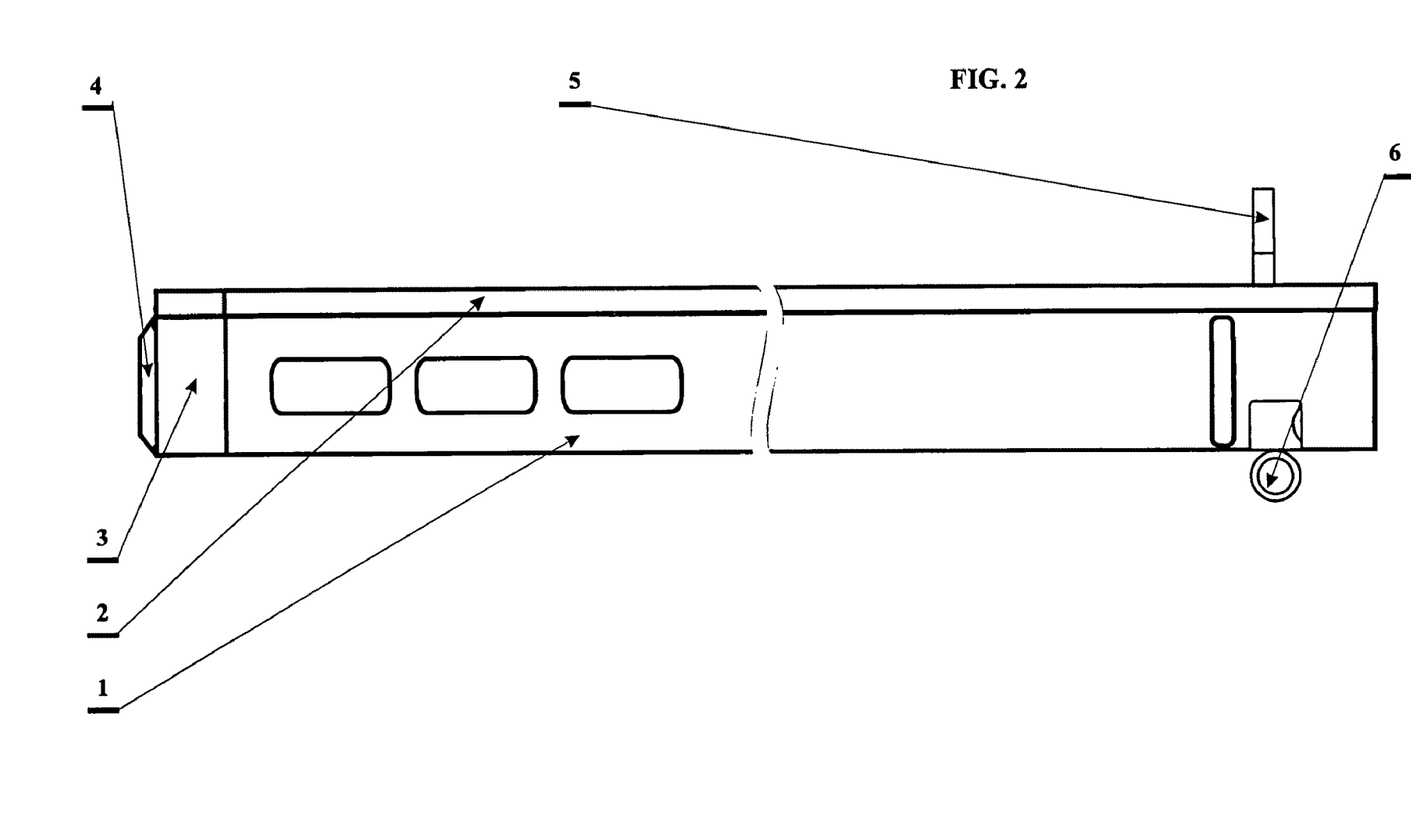
FIG. 2 presents the side view of the drainage.
Figure 3:
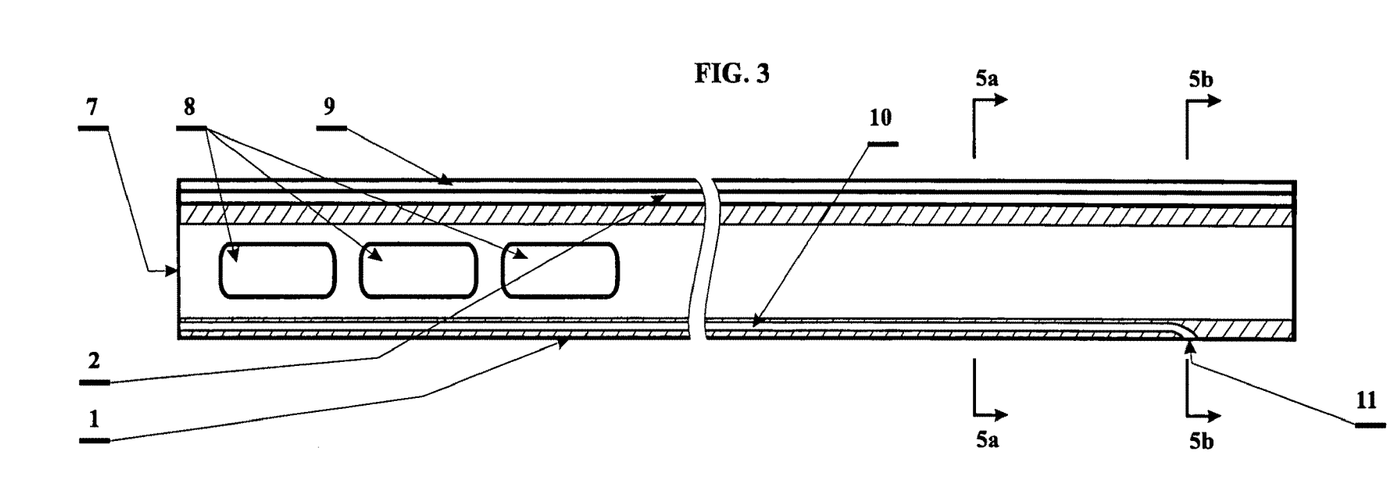
FIG. 3 presents the longitudinal section of the tube drainage.
Figure 4:
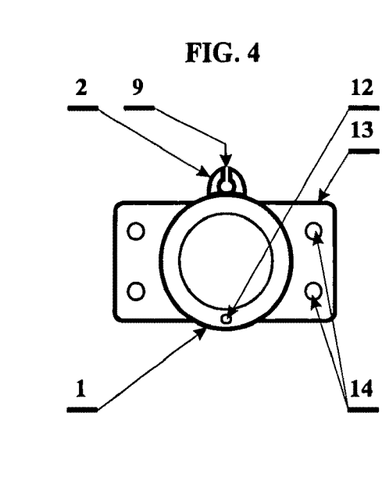
FIG. 4 presents the front view of the tube drainage.
Figure 5:
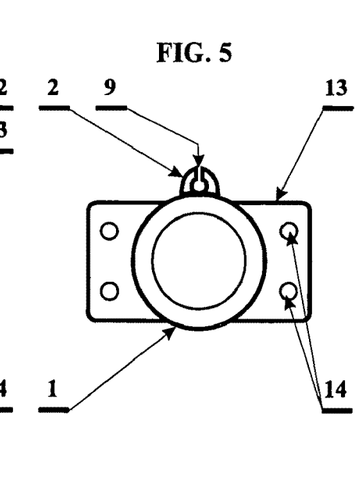
FIG. 5 presents the back view of the tube drainage.
Figure 5A:
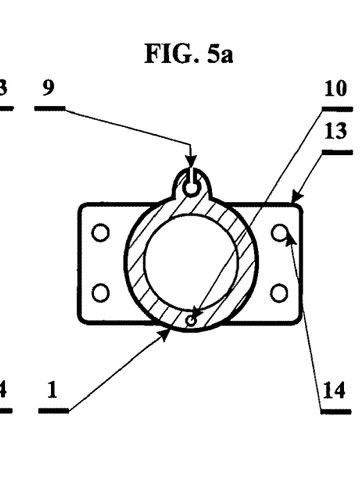
Figure 5B:
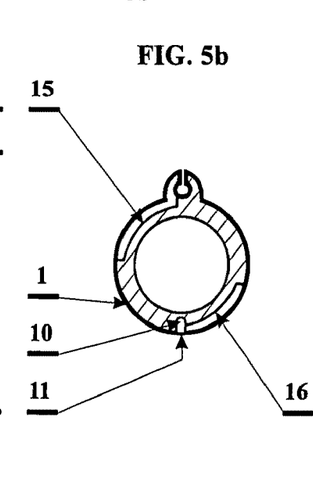
FIG. 5b presents the cross section view of the tube drainage 5b.
Figure 6:
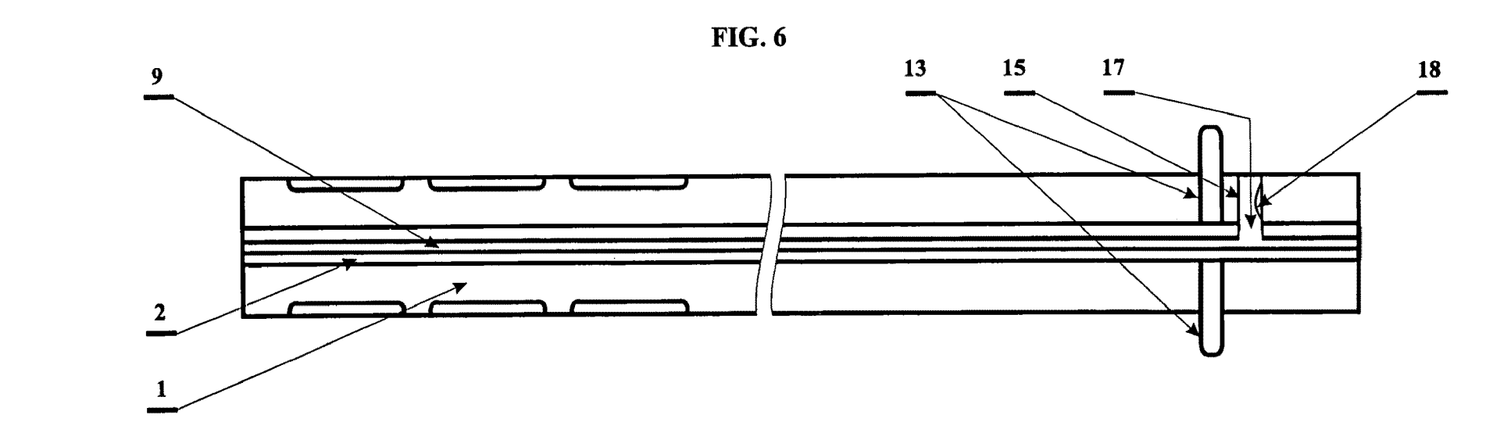
FIG. 6 presents the upper view of the tube drainage.
Figure 7:
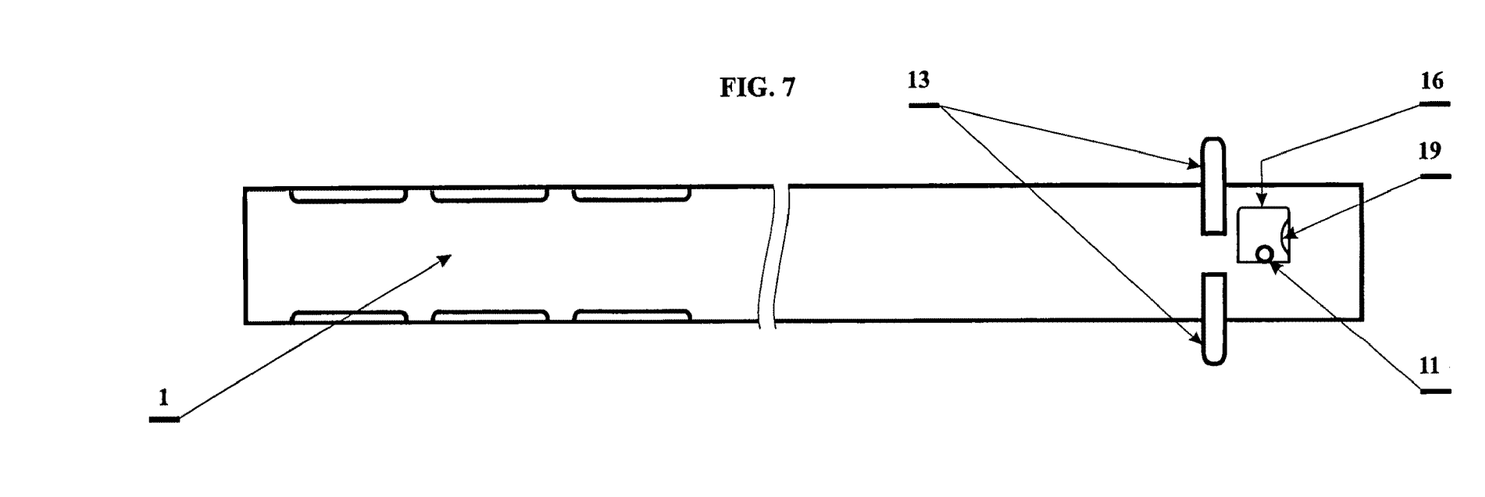
FIG. 7 presents the bottom view of the tube drainage.
Figure 8:
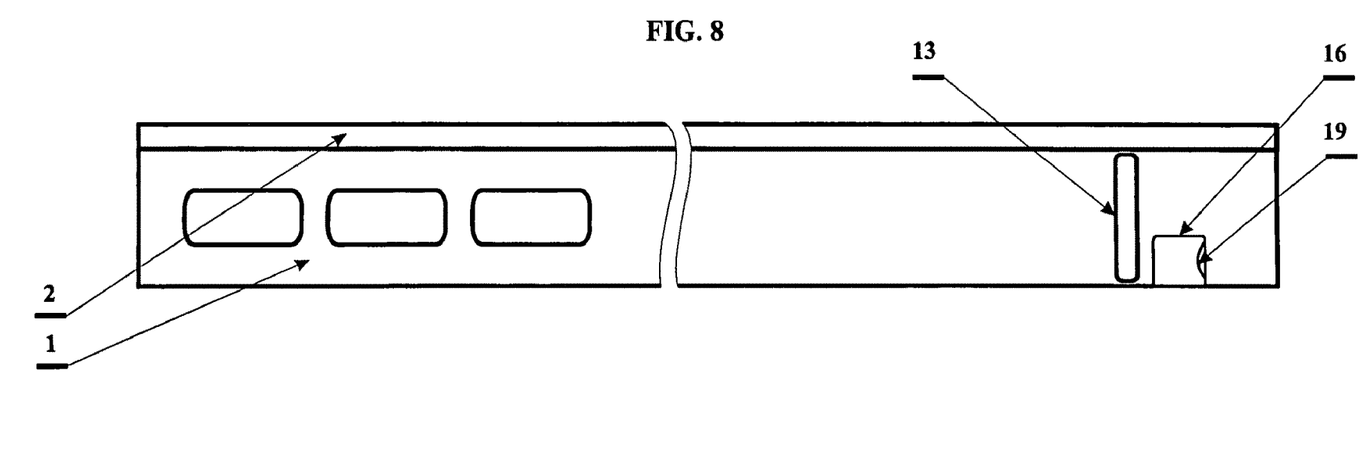
FIG. 8 presents the side view of the tube drainage, pictured from the side of the slot of the splitter's fixing element.
Figure 9:
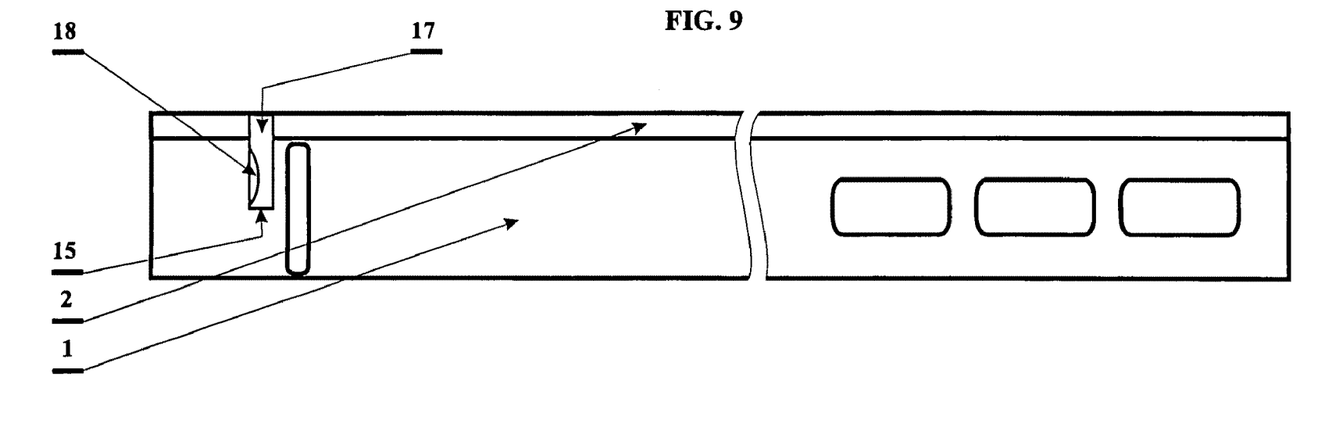
FIG. 9 presents the side view of the tube drainage, pictured from the side of the slot of the conductor.
Figure 10:
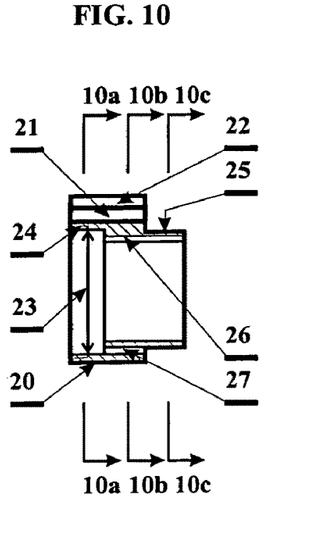
FIG. 10 presents the cross section view of the cylinder of the clots' splitter unit.
Figure 10A:
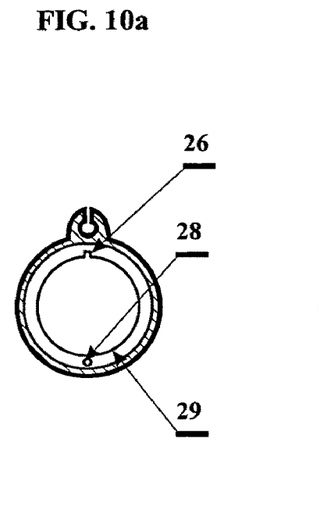
FIG. 10a presents the view of the cylinder of the clots splitter unit in 10a section.
Figure 10B:
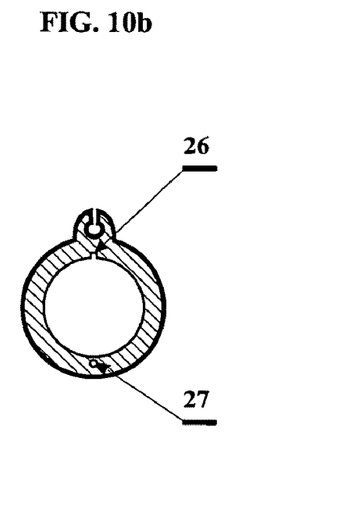
FIG. 10b presents the view of the cylinder of the clots splitter unit in 10d section, FIG. 10c the view of the cylinder of the clots splitter unit in 10c section.
Figure 11:
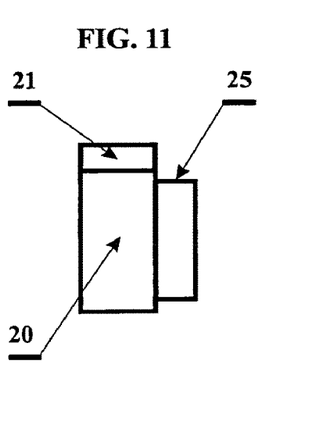
FIG. 11 presents side view of the cylinder of the clots splitter unit.
Figure 12:
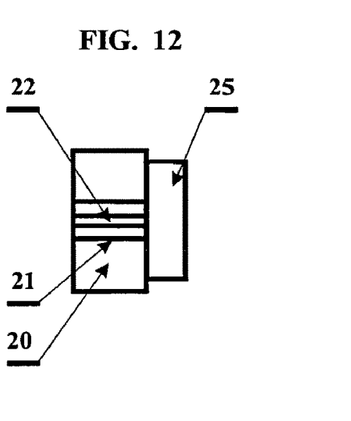
FIG. 12 presents the top view of the cylinder of the clots splitter unit.
Figure 13:
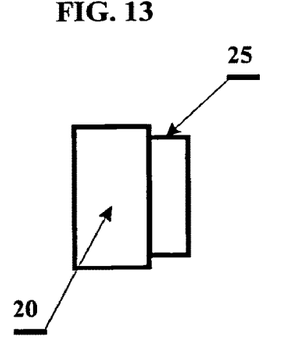
FIG. 13 presents the bottom view of the cylinder of the clots splitter unit.
Figure 14:
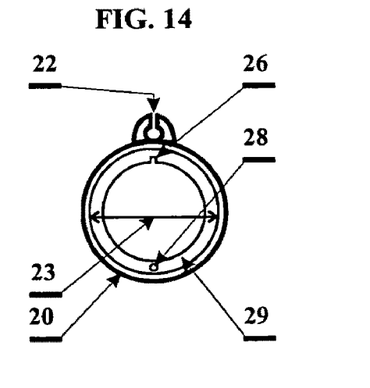
FIG. 14 presents the front view of the cylinder of the clots splitter unit.
Figure 15:
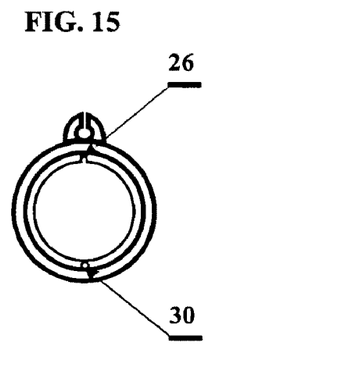
FIG. 15 presents the back view of the cylinder of the clots splitter unit.
Figure 16:
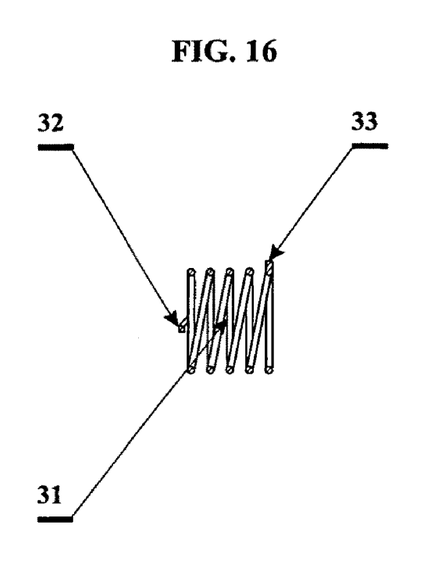
FIG. 16 presents the view of the spring with the clots splitter in longitudinal section.
Figure 17:
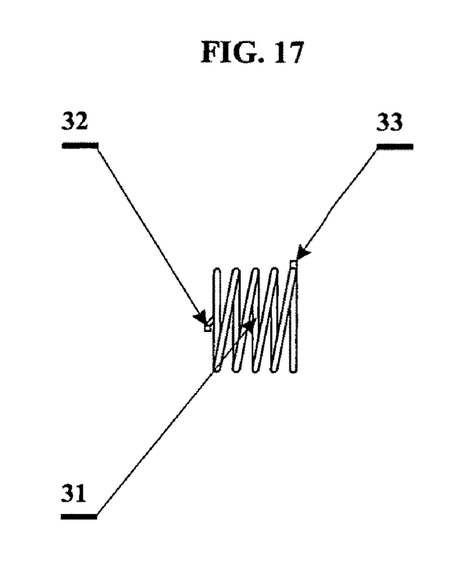
FIG. 17 presents the side view of the spring with the clots splitter.
Figure 18:
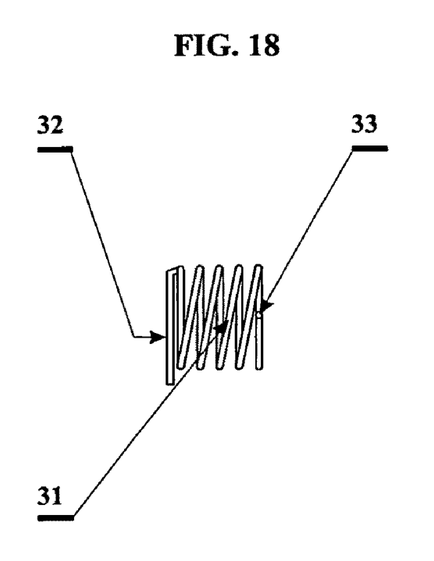
FIG. 18 presents the top view of the spring with the clots splitter.
Figure 19:
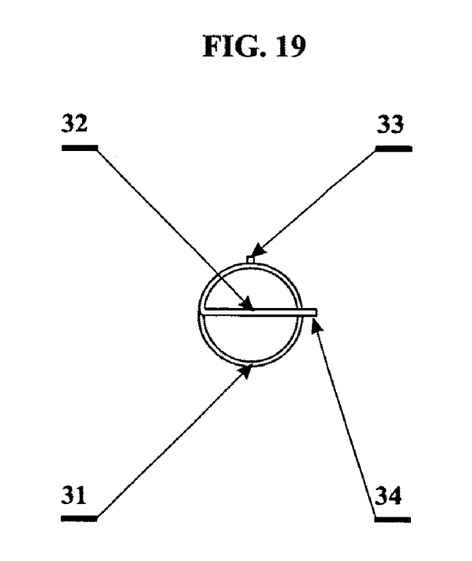
FIG. 19 presents the front view of the spring with the clots splitter.
Figure 20:
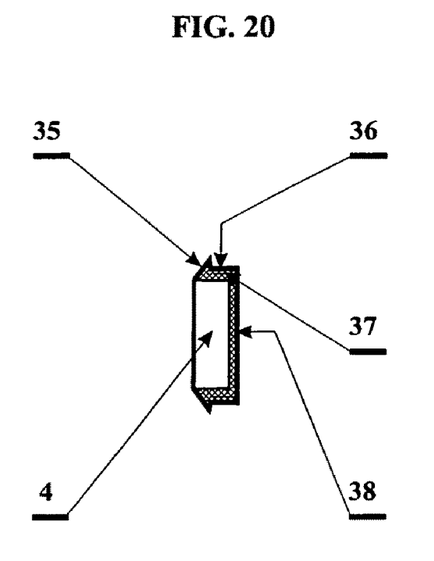
FIG. 20 presents the cross-sectional view of the working head.
Figure 21:
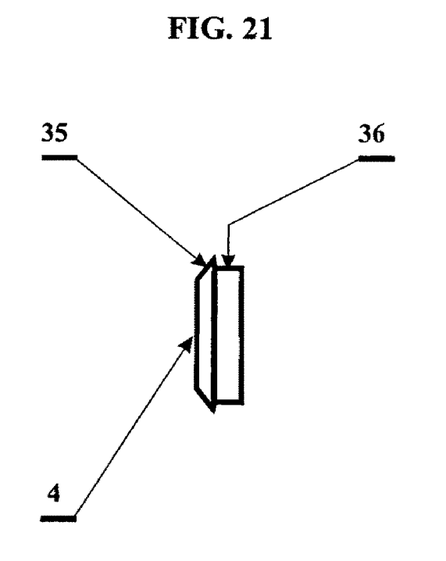
FIG. 21 presents the side view of the working head.
Figure 22:
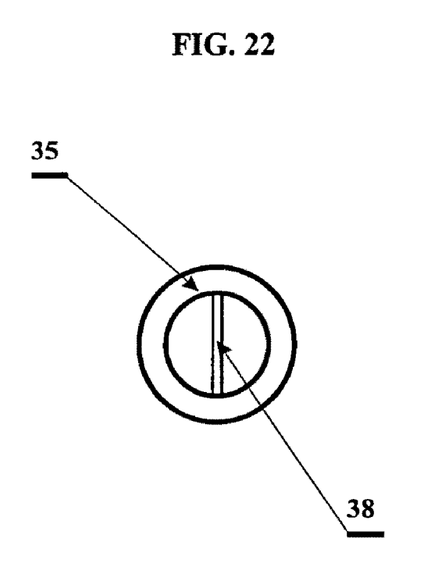
FIG. 22 presents the front view of the working head.
Figure 23:
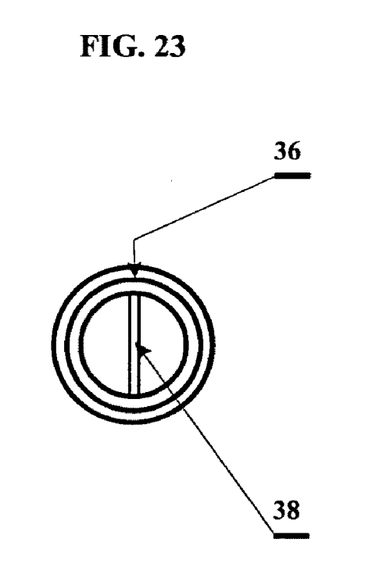
FIG. 23 presents the back view of the working head.
Figure 24:
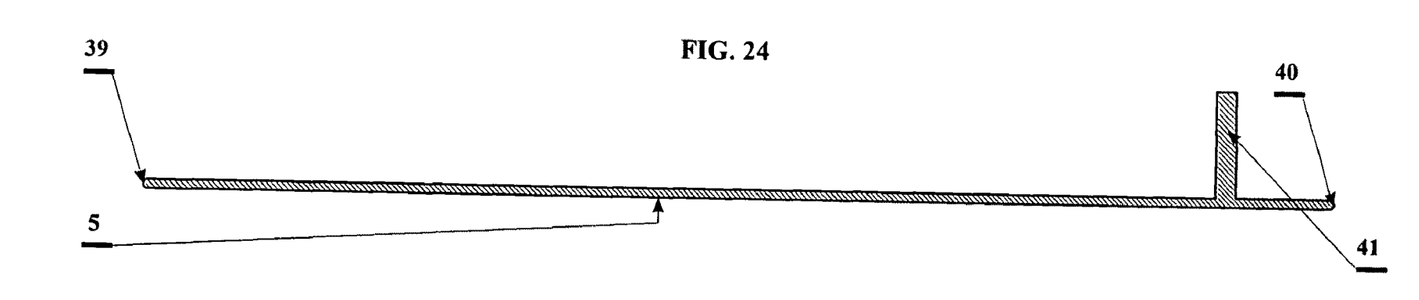
FIG. 24 presents the cross-sectional view of the conductor.
Figures 25, 26:
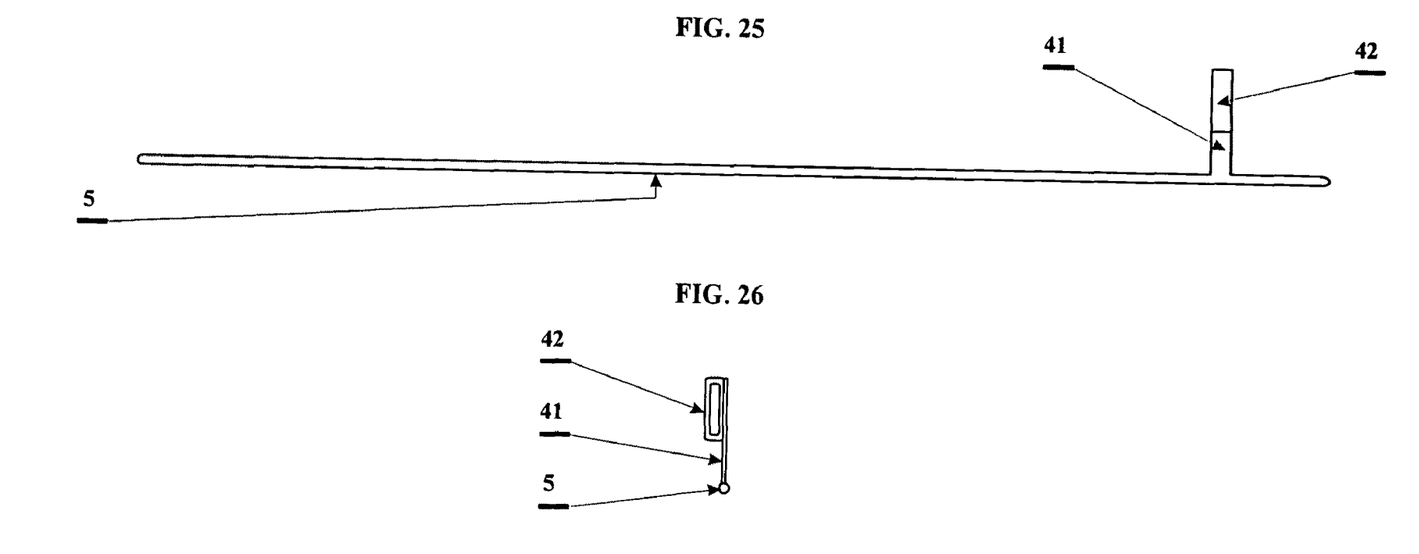
FIG. 25 presents the side view of the conductor.
FIG. 26 presents the back view of the conductor.

The conductor 5 (FIG. 24-FIG. 26) presents a flexible rod of a round cross section, made of dense, elastic material and possesses a working end 39 and a leading end 40. Both ends are rounded. The rounded working end 39 eliminates the possibility of tissues injury, when drainage is replaced. The plate 41 is fixed on the conductor on the side of the leading end 40, a handle 42 being mounted on it. The diameter of the conductor 5 is equal to the internal diameter of the additional tube 2 and the internal diameter of the tube of the clots splitter's unit 21. The plate's thickness 41 of the conductor 5 is equal to the width of an opening 9 of the additional tube 2 and an opening 22 of the tube 21 of the clots splitter's unit, while the plate's 41 height and width correspond to dimensions of the lot 15, made on the body of the tube drainage 1.

Figure 27:
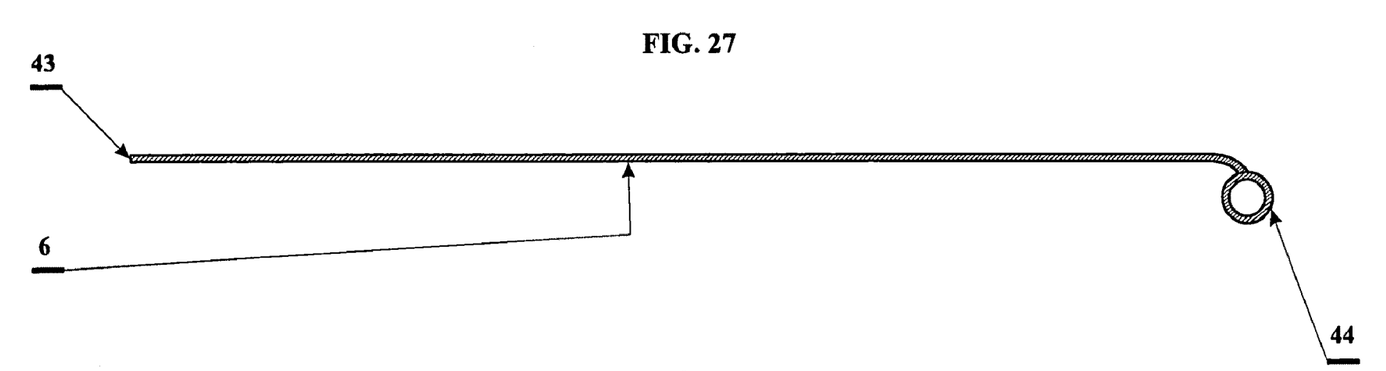
FIG. 27 presents the splitter's fixing element in longitudinal section.
Figures 28, 29:
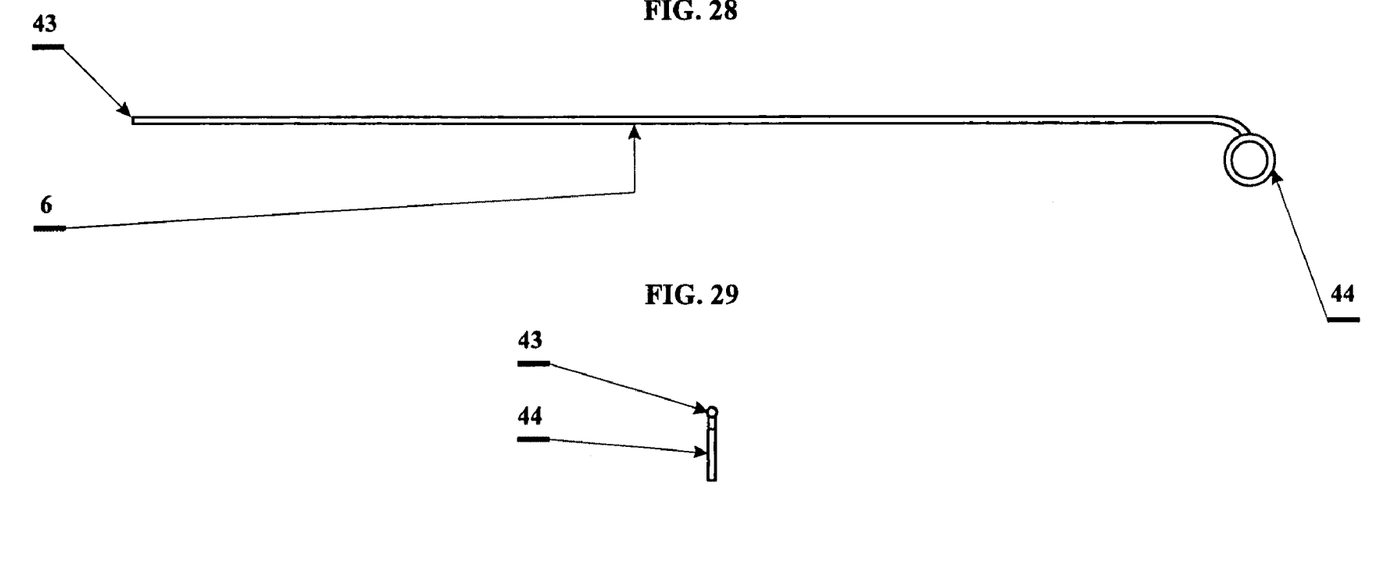
FIG. 28 presents the side view of the splitter's fixing element.
FIG. 29 presents the front view of the splitter's fixing element.
Figure 30:
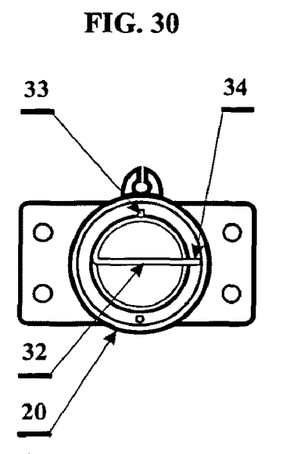
FIG. 30 presents the front view of the clots splitter's unit after the spring with the splitter were inserted into the cylinder of the clots splitter's unit.
Figure 31:
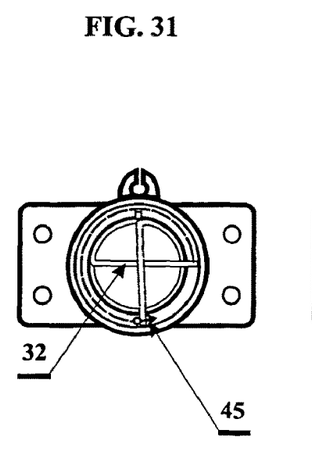
FIG. 31 presents the front view of the clots splitter's unit at the moment when the splitter is turned in a counter-clockwise direction.
Figure 32:
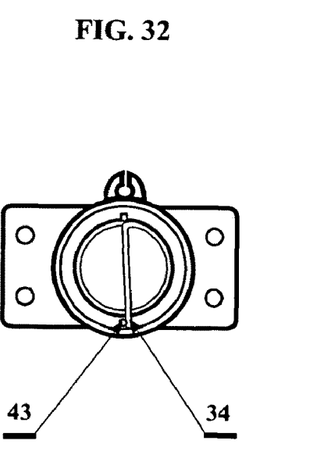
FIG. 32 presents the front view of the clots splitter's unit after the splitter was turned and was fixed anew by the protruded fixing element.
Figure 33:
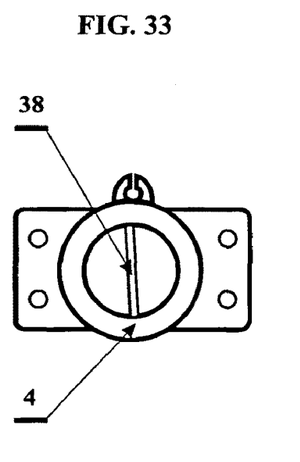
FIG. 33 presents the front view of the drainage with installed working head, after the splitter was turned and was fixed anew by the protruded fixing element.
Figure 34:
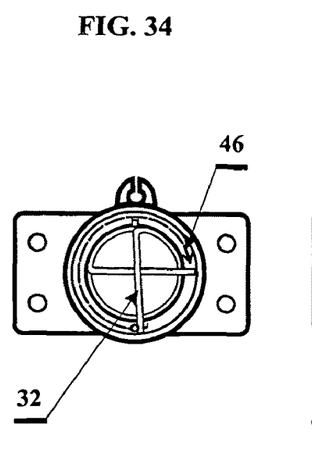
FIG. 34 presents the front view of the clots splitter unit, pictured at the moment, when the splitter is returned into the previous position, after removal of the splitter's fixing element.
Figure 35:
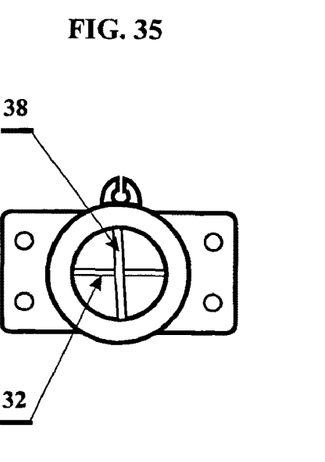
FIG. 35 presents the front view of the drainage with the working head installed after the clots splitter was returned into its previous position.
Figure 36:
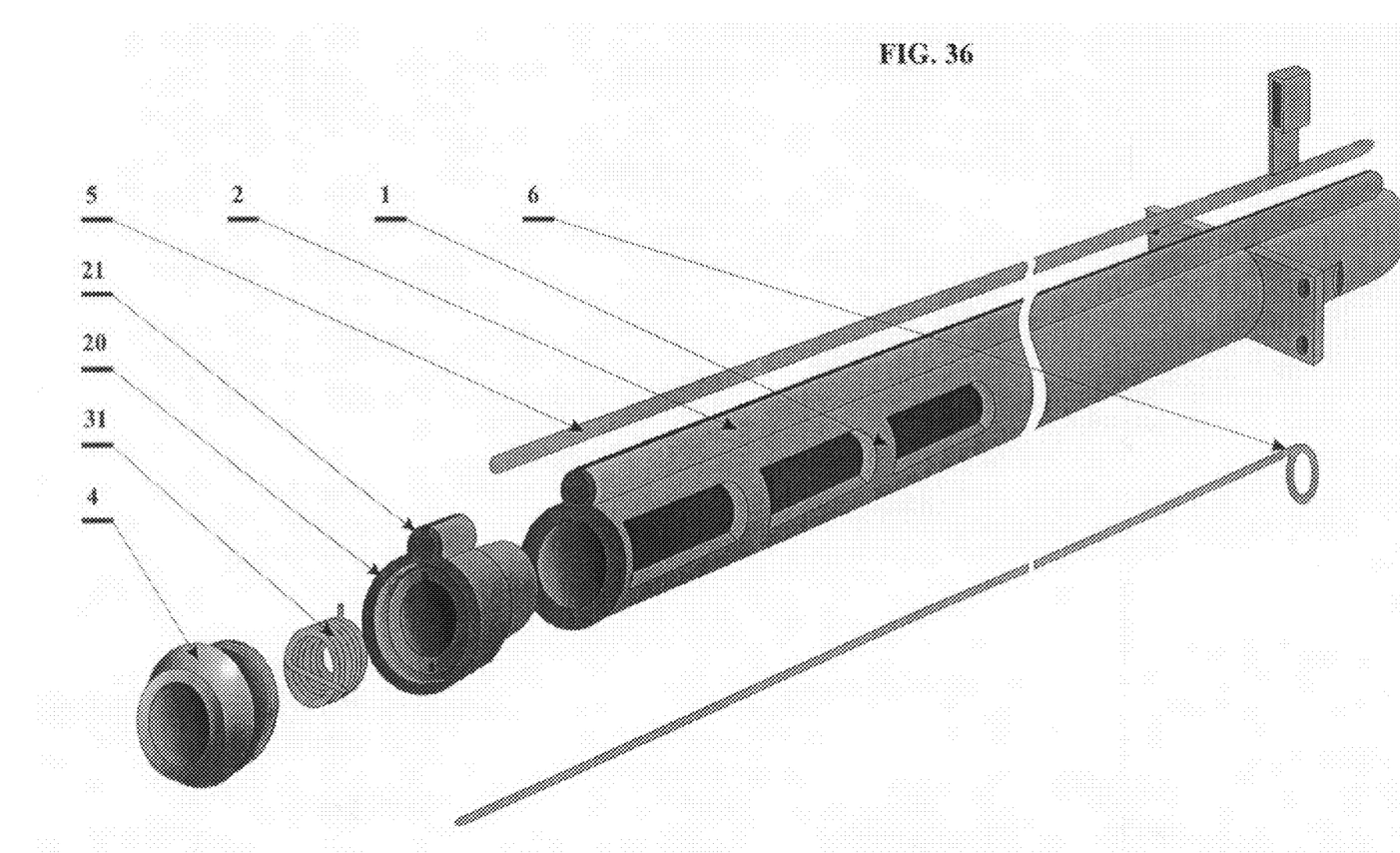
FIG. 36 presents the general view of the drainage, disassembled, in its isometric view.

The splitter's fixing element 6 presents a flexible rod of a round cross section, it is made of a dense and elastic material its working end 43 has a flat butt (FIG. 27-FIG. 29). A ring 44 is fixed on the opposite end of the fixing element 6.

The drainage system and its elements may be made of the following materials: tubical drainage, additional tube made from medical silicone, block for clot cutting, working head, conductor, holder of cutter, cutter is made from medical steel.

The drainage works in the following way. Before a surgical operation drainage is put into the working state. For this purpose a body of the clots splitter's unit 20 is inserted into the tube drainage on the side of its working end 7. The uniform diameter of the external growing-through 25 of the body 20 the clots splitter's unit and the internal diameter of the tube drainage 1 ensure their dense contact and fixing of the body 20 in the tube drainage. The body 20 being orientated in such a way, so that an opening of the additional tube 2, fixing on the tube drainage should coincide with the opening of the tube 21 of the clots splitter's unit and the opening 12 of the channel 10 of the splitter's fixing element, made inside the wall of the tube drainage should coincide with the opening 30 of the channel 27 of the body. A spring 31 is inserted into the body 20 in such a way, so that the spring's fixing element should pass into the slot 26 of the clots splitter's unit. The clots splitter 32 here will be located inside the body 20 on the level of the internal growing-through 23 of the body (See FIG. 30-FIG. 35). Through the opening 11, made on the external surface of the tube drainage 1 a fixing element of the splitter 6 is inserted and it is passed to the wall of the tube drainage through the channel 10 and channel 27, made inside the body up to the level, when the working end 43 of the fixing element is on the level of the opening 28 of the body's channel on the side of its internal growing through. Clots (32) splitter 45 is turned by 270° angle in a counter-clockwise direction. The protruding end of the splitter 34 should be located behind the opening 28 of the body's channel. Holding the clots splitter 32 in such position, the splitter's fixing element 6 is moved in such a way, so that its working end 43 should keep the protruding end 34 of the splitter 32 in that position.

A working head 4 is inserted into the body 20 so that the thread 37 of the external growing-through of the head 36 should combine with the internal thread 24 of the internal growing-through 23 of the body. The 4 is turned in such a way, so the rod 38 of the working head 4 should be placed parallel with the clots splitter 32. The splitter's ring 44 is turned, so that it will go into the slot 16, made on the external surface of the tube surface. By placing the splitter's ring into the slot 16 a stable position of the working end of the fixing element 43 is ensured and consequently clots splitter 32 can be kept reliably in the desired position.

The splitter's ring 44 is kept inside the slot 16 by means of a latch 19. Then a conductor 5 is inserted into the gap of the additional tube 2, from the side of the opposite head and it is led throughout the entire additional tube 2 and the tube 21 of the unit of clots splitter. The conductor's plate 41 being led through the opening 9 of the additional tube and is to be placed opposite to the growing-through 17 inside the additional tube 2 and slot 15. After that the conductor's plate 41 is turned and inserted into the slot 15, where it is eventually fixed with a latch 18. The location of the plate 41 in the slot 15 eliminates the possibility of distortion of the working end during the process of prolong staying of the drainage, thus guaranteeing the precise location of the end of the following drainage installation, which will replace the old one through the conductor 5. Now the drainage is ready for work. The described preparation of drainage can be performed at a plant.

A set of drainage installations, of the design, described here, of equal length with different diameter of tube drainage 1 and the body 20 of the splitter's unit. The diameter of the additional tube 2 and the tube 21 of the clots splitter's unit and also the diameters of the channel 10 of the conductor's fixing element in the tube drainage 1 and the channel of the clots splitter's fixing element in the splitter's unit are equal for all drainage procedures. Only the first drainage set is supplied with the conductor 5.

Drainage is used in the following way. After the surgical operation drainage is inserted into a cavity, which needs to undergo drainage. Drainage is fixed to skin by means of the openings 14, made in the fixing plates 13. Aspiration is carried out in an active or passive way both through the side openings 8 and through the opening in the working head 4. After the drainage system has completed its work due to its obstruction with a clot or a piece of tissue, the system is replaced with a drainage set of smaller diameter. To perform it is necessary to remove drainage coupling to skin, after that the ring 44 of the splitter's fixing element is removed from the slot 16 and by traction through the ring 44, the fixing element 6 is removed from the drainage. This results in the spring's 31 returning to its original location. The clots 32 splitter 46 is turned by 270° angle in a clockwise direction. As the result the clot is cut out between the splitter 32 and the head's rod 38. After the turning the splitter is located perpendicular to the axis of the head's rod 38, thus making it possible to retain the cut out clot inside the drainage opening. The conductor's plate 41 is removed from the slot 15 using the plate's handle 42, after which, holding the conductor in its previous position, the drainage is removed from the cavity by means of the handle 42. Then the leading end 40 of the conductor 5 is inserted into the opening of the tube 21 of the splitter's unit of the new drainage set with smaller diameter of the tube drainage and the new drainage is led up to the level where the old drainage has stood, along the conductor 5. The rounded shape of the leading end 40 facilitates its insertion into the tube's opening 21. The conductor 5 first passes inside the tube of the splitter's unit 21 and then inside the additional tube 2 up to the level of the growing-through 17. After that the conductor's plate 41 is turned and it is placed into the slot 15, where it is fixed by means of a latch 18. a new drainage set is coupled to the skin through the openings 14 in the fixing plates 13. Then the cavity undergoes drainage. In case of necessity the new drainage set is replaced by the subsequent sets of smaller diameters, using the methods described above. After the cavity has become smaller, as well as the diameter of the wound channel it may be possible to leave only the conductor 5 inside, which could be used for subsequent insertion of drainage a few days later. In case the conductor 5 is remained in the cavity it is to be fixed to the skin through the handle 42. Besides, in case the drainage has to stand for a long time it is possible to replace the conductor 5, prior to the removal of the last drainage.

The invention claimed is:
1. A drainage, comprising
a main tube with a working end and side and butt openings and an external surface,
an additional tube of a smaller diameter with an opening, fixed rigidly along the main tube,
a conductor, installed inside the additional tube,
a clots splitter unit, placed on the working end of the main tube,
said unit comprising a housing, a short tube on an external surface of the housing with an opening on the short tube, corresponding to the opening of the additional tube and a spring with a cutter, installed inside the housing, a working head with a rod connected with the housing of the clots splitter unit,
wherein a wall of the main tube and a wall of the clots splitter unit comprising a channel, inside said channel located a splitter fixing unit, said splitter fixing unit comprising a working end and opposite end, said working end being inside the clots splitter unit and fixes the cutter, while the opposite end of the splitter fixing unit is led through the channel and equipped with a ring.

2. The drainage in accordance with claim 1, wherein the working head coupled with the housing of the splitter by thread connection.

3. The drainage in accordance with claim 1, wherein the channel of the splitter being located on the side opposite to a side where the additional tube and the tube of the clot splitter's unit are fixed, respectively and the channel of the splitter's unit, made inside the splitter's unit is opened by in an internal opening on a surface of a ledge's ring, formed by a difference in a diameter of an internal growing and a housing internal diameter.

4. The drainage in accordance with claim 1, wherein an outside diameter of the spring is about to an internal diameter of the clots splitter's unit, while a diameter and a height of the spring's fixing element are about respectively to a width and a depth of a slot of the housing.

5. The drainage in accordance with claim 1, wherein the cutter fixed to the spring in such a way, so that an axis of the cutter is located at 90° angle towards the axis of the spring's fixing element.

6. A method of drainage of cavities after various surgical operations with a first and all subsequent drainage sets of claim 1 and comprising following steps:

inserting a first drainage into the cavity, which has to undergo drainage and coupling the drainage to skin, performing aspiration;

replacing the first drainage by a second drainage of a smaller diameter after functioning of the first drainage is stopped because its opening became blocked by a clot or pieces of tissue, a second drainage of a smaller diameter being installed by means of removing of fixation of the first drainage to the skin, cutting out of the clot and keeping the cut out clot inside the drainage opening and by holding the conductor in its original position with the handle, then removing the first drainage from the cavity and the leading end of the conductor is inserted into the opening of the splitter's unit's tube and the second drainage is installed with a smaller diameter, which is led up to the level of the first drainage along the conductor.

* * * * *